US011730426B2

(12) United States Patent
Hjelle et al.

(10) Patent No.: US 11,730,426 B2
(45) Date of Patent: Aug. 22, 2023

(54) CATHETER WITH SEGMENTED ELECTRODES AND METHODS OF MAKING SAME

(71) Applicants: Heraeus Medical Components LLC, St. Paul, MN (US); Heraeus Deutschland GmbH & Co. KG, Hanau (DE)

(72) Inventors: Mark A. Hjelle, Fridley, MN (US); Katharina Musiol, Aschaffenburg (DE); Christiane Leitold, Woelfersheim (DE)

(73) Assignees: Heraeus Medical Components LLC, St. Paul, MN (US); Heraeus Deutschland GmbH & Co. KG, Hanau (DE)

( * ) Notice: Subject to any disclaimer, the term of this patent is extended or adjusted under 35 U.S.C. 154(b) by 1057 days.

(21) Appl. No.: 16/527,887

(22) Filed: Jul. 31, 2019

(65) Prior Publication Data

US 2020/0037957 A1    Feb. 6, 2020

Related U.S. Application Data

(60) Provisional application No. 62/712,423, filed on Jul. 31, 2018.

(51) Int. Cl.
*A61B 5/00* (2006.01)
*A61M 25/00* (2006.01)

(52) U.S. Cl.
CPC ....... *A61B 5/6852* (2013.01); *A61M 25/0012* (2013.01); *A61M 25/0015* (2013.01);
(Continued)

(58) Field of Classification Search
CPC .......... A61M 25/0012; A61M 25/0015; A61M 25/0029; A61M 25/0054; A61B 5/6852;
(Continued)

(56) References Cited

U.S. PATENT DOCUMENTS

| 5,788,692 A | 8/1998 | Campbell et al. |
| 6,430,425 B1 | 8/2002 | Bisping |

(Continued)

FOREIGN PATENT DOCUMENTS

| CN | 1 730 121 | 2/2006 |
| CN | 107148249 | 9/2017 |

(Continued)

*Primary Examiner* — Rebecca E Eisenberg
*Assistant Examiner* — Justin L Zamory
(74) *Attorney, Agent, or Firm* — Dicke, Billig & Czaja, PLLC

(57) ABSTRACT

Aspects of the disclosure relate to medical catheters, including electrophysiological catheters, comprising a catheter maintaining at least one electrode including a plurality of electrode segments. The catheter can include a plurality of slots in which the electrodes can be secured so that the electrodes are at least partially positioned within a center lumen of the catheter. Methods of manufacturing medical catheters are also disclosed. In various methods of assembling a catheter, a hollow, tubular catheter made of a compliant material having a very small, micro or nano outside diameter is provided. Then, the slots are formed in the catheter and the electrode segments are positioned within the slots.

20 Claims, 3 Drawing Sheets

(52) U.S. Cl.
CPC .... *A61M 25/0029* (2013.01); *A61M 25/0054* (2013.01); *A61B 2562/125* (2013.01)

(58) Field of Classification Search
CPC .......... A61B 2562/125; A61B 2562/02; A61B 2018/1497; A61N 1/0476; A61N 1/05
See application file for complete search history.

(56) References Cited

U.S. PATENT DOCUMENTS

| | | | |
|---|---|---|---|
| 6,882,879 B2 | 4/2005 | Rock | |
| 8,019,440 B2 | 9/2011 | Kokones et al. | |
| 8,225,504 B2 | 7/2012 | Dye et al. | |
| 8,560,074 B2 | 10/2013 | McDonald | |
| 8,649,879 B2 * | 2/2014 | DiGiore | A61N 1/0551 607/116 |
| 8,700,179 B2 | 4/2014 | Pianca et al. | |
| 8,828,201 B2 | 9/2014 | Simpson et al. | |
| 8,868,206 B2 | 10/2014 | Barker et al. | |
| 8,923,982 B2 | 12/2014 | Howard | |
| 9,248,275 B2 | 2/2016 | DiGiore et al. | |
| 9,248,277 B2 | 2/2016 | Chen | |
| 9,289,596 B2 | 3/2016 | Leven | |
| 9,364,286 B2 | 6/2016 | Werneth et al. | |
| 9,517,103 B2 | 12/2016 | Panescu et al. | |
| 9,555,234 B2 | 1/2017 | Duijsens et al. | |
| 9,775,988 B2 | 10/2017 | Govea et al. | |
| 2008/0114230 A1 | 5/2008 | Addis | |
| 2011/0078900 A1 | 4/2011 | Pianca et al. | |
| 2011/0245903 A1 | 10/2011 | Schulte et al. | |
| 2011/0275951 A1 * | 11/2011 | Lips | A61B 5/287 600/547 |
| 2015/0196356 A1 * | 7/2015 | Kauphusman | A61B 18/1492 606/41 |
| 2018/0042506 A1 | 2/2018 | Locke et al. | |

FOREIGN PATENT DOCUMENTS

| | | |
|---|---|---|
| EP | 1 174 080 | 1/2002 |
| JP | 2016 137020 | 8/2016 |

* cited by examiner

CATHETER WITH SEGMENTED ELECTRODES AND METHODS OF MAKING SAME

CROSS-REFERENCE TO RELATED APPLICATIONS

This application is a Non-Provisional of U.S. application Ser. No. 62/712,423, filed Jul. 31, 2018, which is herein incorporated by reference.

TECHNICAL FIELD

This disclosure relates to segmented electrodes configured for sensing and/or stimulation within a biological application.

BACKGROUND

In some embodiments, ring electrodes are provided on the distal end of a catheter for sensing or stimulation within a human body. The distal end of a catheter is placed adjacent tissue that is to be sensed or stimulated and the ring electrodes either transmit or receive energy. In some cases, it is useful to have very discrete locations energized, and accordingly, use only a segment of a ring electrode, rather than the entire ring. Manufacturing discrete electrode segments can be difficult, particularly where multiple electrode segments are desired on a small diameter catheter. For these and other reasons, there is a need for the present disclosure.

SUMMARY

One aspect is a medical catheter having a catheter body made of a compliant material. The catheter body has a center lumen and includes first and second slots. The medical catheter includes a first electrode having a plurality of electrode segments, each electrode segment including a contact surface interconnecting first and second retaining features. The contact surface and the first and second retaining features collectively define a channel. The first retaining feature is within the first slot and the center lumen of the catheter and the second retaining feature is within the second slot and the center lumen so that the catheter body is positioned within the channel.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims. It is also to be understood that the features of the various exemplary embodiments described herein may be combined with each other, unless specifically noted otherwise.

Figure 1:
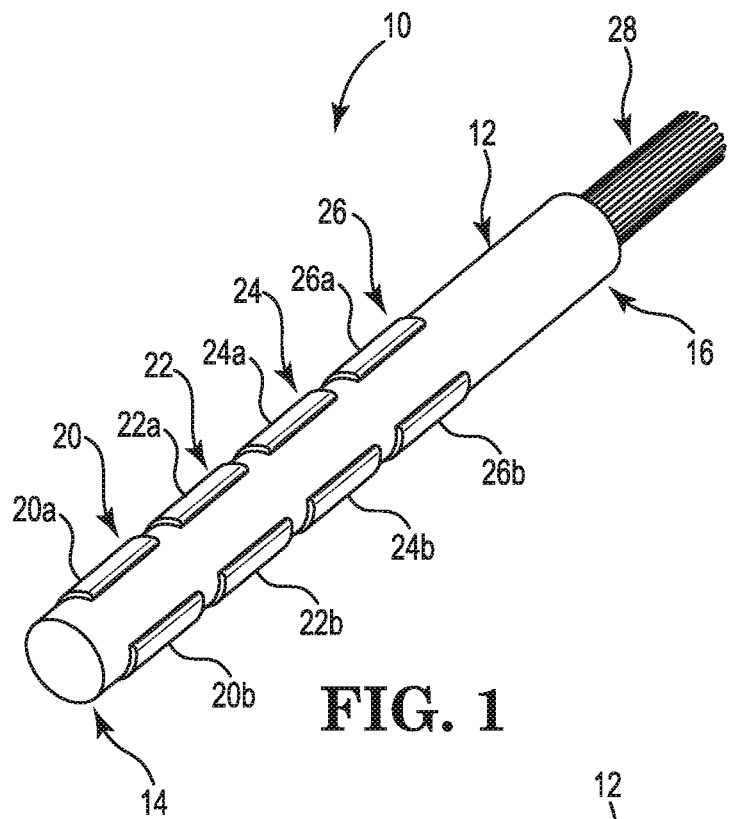
FIG. 1 illustrates a perspective view of a medical catheter including a catheter body supporting segmented electrodes and a wiring assembly in accordance with one embodiment.
Figure 2:
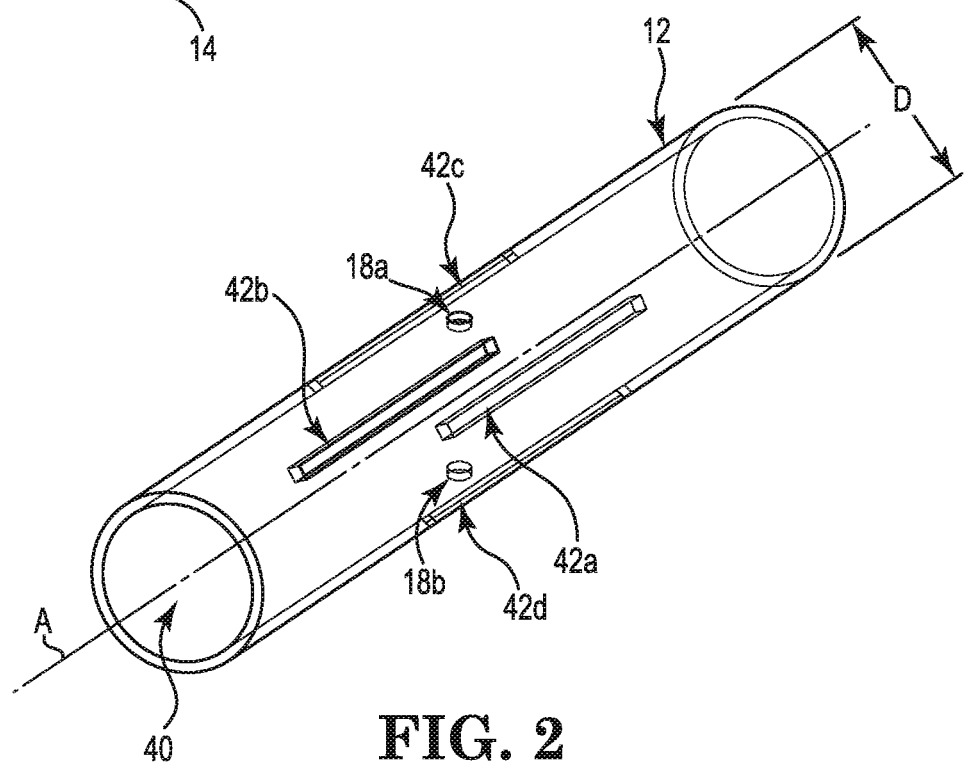
FIG. 2 illustrates a perspective view of a portion of the catheter body of FIG. 1 having a plurality of slots in accordance with one embodiment (the catheter body is shown as transparent for ease of illustration).
Figure 3:
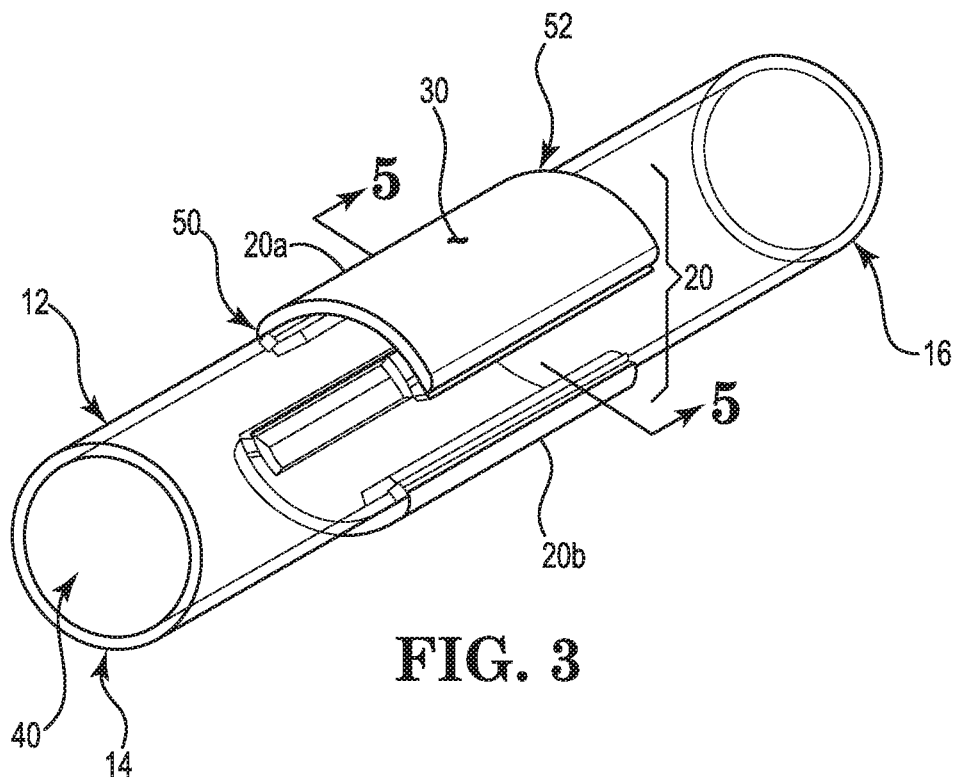
FIG. 3 illustrates a perspective view of the catheter body of FIGS. 1-2 including an electrode having segmented electrodes secured within the slots visible in FIG. 2 (the catheter body is shown as transparent for ease of illustration).
Figure 4:
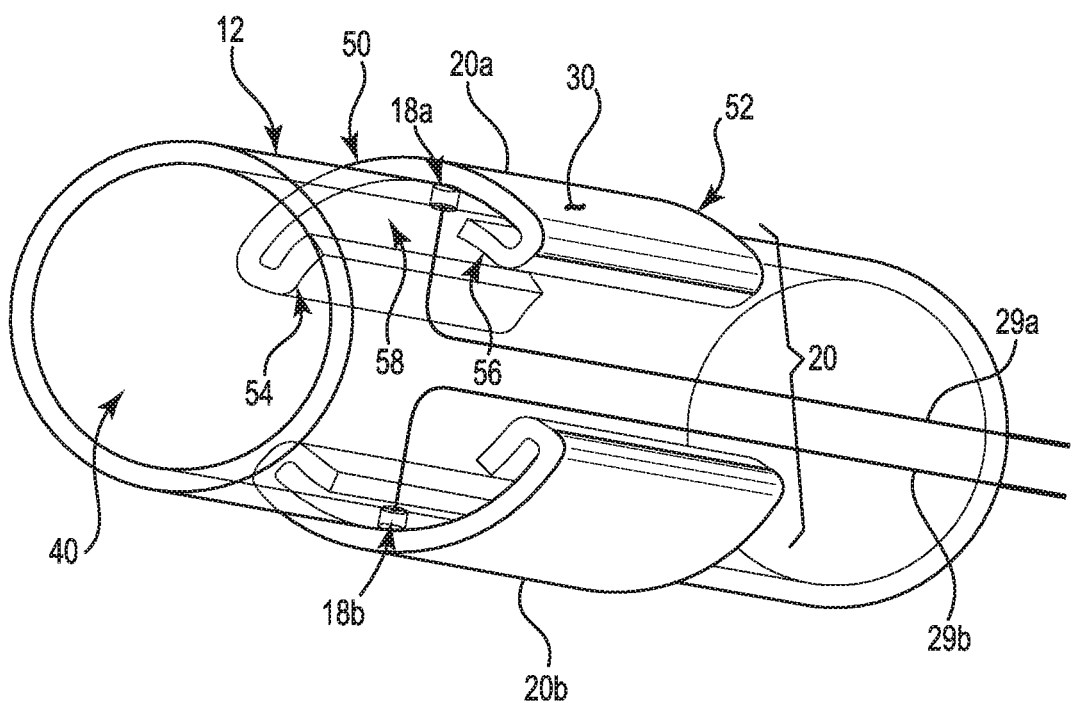
FIG. 4 illustrates an alternate perspective view of the catheter body and segmented electrodes of FIG. 3 (the catheter body is shown as transparent for ease of illustration).

FIGS. 1-6 illustrate components of a medical catheter 10. FIG. 1 illustrates a perspective view of the medical catheter 10 of one embodiment having a catheter body 12 including a distal end 14 and proximal end 16. It is noted that the catheter body 12 is shown as transparent in FIGS. 2-4 for ease of illustration and is not necessarily transparent in practice (see, e.g., FIG. 1). At the distal end 14 of the catheter body 12, the catheter 10 includes a plurality of electrodes 20, 22, 24, 26 each having a plurality of independently accessible electrode segments 20a-b, 22a-b, 24a-b, 26a-b. The electrodes 20, 22, 24, 26 are operatively connected to a wiring assembly 28 configured to allow for independent electrical control of each of the electrode segments 20a-b, 22a-b, 24a-b, 26a-b provided in any known manner. In one illustrative embodiment, the wiring assembly 28 includes a plurality of flexible, insulated conductors (only a representative few of which are referenced for ease of illustration; e.g., 29a, 29b as are seen in FIG. 4), one conductor 29a, 29b for each electrode segment 20a-b, 22a-b, 24a-b, 26a-b. Each conductor 29a, 29b can be routed through a lumen 40 of the catheter body 12. From the lumen 40, each conductor 29a, 29b is threaded through one respective aperture 18a, 18b formed in the catheter body 12 to one respective electrode segment 20a-b, 22a-b, 24a-b, 26a-b. Alternatively, the conductors 29a, 29b of the wiring assembly 18 can be formed as conductive traces that are printed on the outside of the catheter body 12 to provide more available space within the center lumen 40 of the catheter body 12 to improve torque, repeatable distal deflection, force sensing or to optionally use the center lumen 40 for housing force sensors or irrigation, for example. The number of electrodes 20, 22, 24, 26 and segments 20a-b, 22a-b, 24a-b, 26a-b provided for each electrode 20, 22, 24, 26 can vary in alternate embodiments.

In operation, the catheter 10 may be configured for use within a human body. Once within a human body, each of the electrode segments 20a-b, 22a-b, 24a-b, 26a-b may be used for directional stimulation or for positional feedback sensing. Rather than using a single ring electrode that spans the entire 360° circumference of a catheter, the catheter 10 includes electrodes 20, 22, 24, 26 each having two or more electrode segments 20a-b, 22a-b, 24a-b, 26a-b that span only a portion of the circumference of the catheter body 12 (for example, 180°, 120°, 90° degrees or less) such that directional stimulation or positional feedback sensing can be much more precisely controlled relative to a given target within the human body. Various embodiments described herein are particularly useful to enhance the diagnostics and treatment of arrhythmias to provide shorter procedures and potentially improved clinical outcomes and also allow for the manufacture of catheters having increased density of electrode segments. Increased density of electrode segments is useful in a variety of applications, particularly electrophysiology catheters.

In one embodiment, the manufacture of catheter 10 begins with providing catheter body 12. The catheter body 12 is generally a hollow tube having center lumen 40 and also has a very small, micro or nano outside diameter D, for example, the diameter D is as small as about 7 French (0.0945 inches) or less. Catheter body 12 can be made of any of a variety of materials, and in one embodiment is compliant and made of a material such as polyether block amide (also known as PEBA or PEBAX®) or the like, for example. In other embodiments, the catheter body 12 can be made of stainless steel, wire or fiber. The catheter body 12 material can be braided or solid. In embodiments where catheter body 12 is manufactured from such compliant or flexible materials and in such miniaturized dimensions, forming electrode segments cannot be achieved with conventional techniques, such as over-molding, reflow and centerless grinding techniques as described, for example, in Published U.S. Patent Application No. US20180042506-A1.

Accordingly, in one embodiment, the catheter body 12 is manufactured to include a plurality of slots 42a-d (only a few of which are referenced in FIG. 2) extending along its length and parallel to a center axis A of the lumen 40 and through the entirety of the material of the catheter body 12 such that each electrode segment 20a-b, 22a-b, 24a-b, 26a-b can be positioned at least partially outside of the catheter body 12 and at least partially inside the central lumen 14, while being maintained within two respective slots (e.g., 42a, 42b). Additionally, the apertures 18a, 18b can be formed by the same process as the slots 42a, 42b or can be manufactured in a separate or differing process. The apertures 18a, 18b can also be formed via drilling, punching or otherwise. As indicated above, the number of slots 42a 42b and apertures 18a, 18b can relate to the number of electrode segments 20a-b, 22a-b, 24a-b, 26a-b to be connected to the catheter 10. For example, if eight electrode segments 20a-b, 22a-b, 24a-b, 26a-b are provided, the catheter body 12 can include sixteen corresponding slots (e.g., 42a) and eight apertures (e.g., 18a). In one example method of assembly, each electrode segment 20a-b, 22a-b, 24a-b, 26a-b is coupled to one conductor (e.g., 29a, 29b) of the wiring assembly 28 that is then strung through one respective aperture 18a, 18b and into the lumen 40 of the catheter body 12, back to the proximal end 16 before the respective electrode segment 20a-b, 22a-b, 24a-b, 26a-b is secured into place within respective slots (e.g., 42a, 42b). Although only four slots 42a-d are visible and referenced in FIGS. 2 and 5, all other slots provided for receiving the electrode segments 20a-b, 22a-b, 24a-b, 26a-b can be identically formed and configured along the length of the catheter body 12. In various embodiments, the slots 42a-d for each electrode 20, 22, 24, 26 are positioned the same distance from the distal end 14 so that each electrode segment 20a-b, 22a-b, 24a-b, 26a-b of each electrode 20, 22, 24, 26 is the same distance from the distal end 14. In one embodiment, each slot 42a-d has a width and a length that is generally equivalent to a length and material thickness of the respective electrode segment to assist in retaining the respective electrode segment within the slot 42a-d. The slots 42a-d and apertures 18a, 18b can be formed via a variety of methods including laser cutting. Other methods are also envisioned in accordance with other embodiments.

Figure 5:
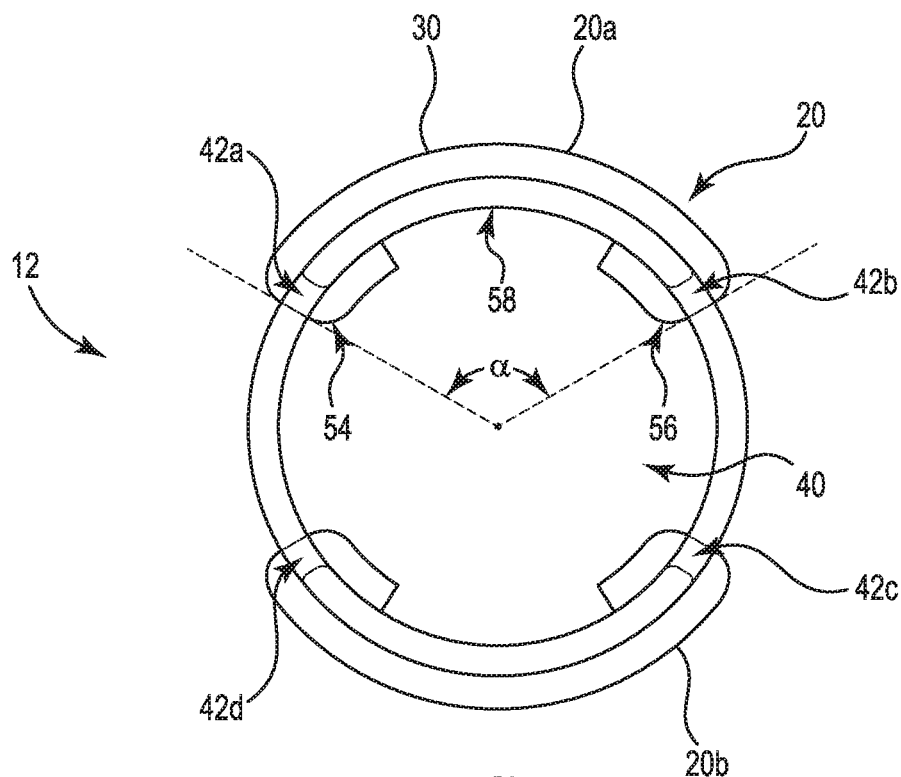
FIG. 5 illustrates a cross-sectional view of FIG. 3 as viewed from line 5-5.
Figure 6:
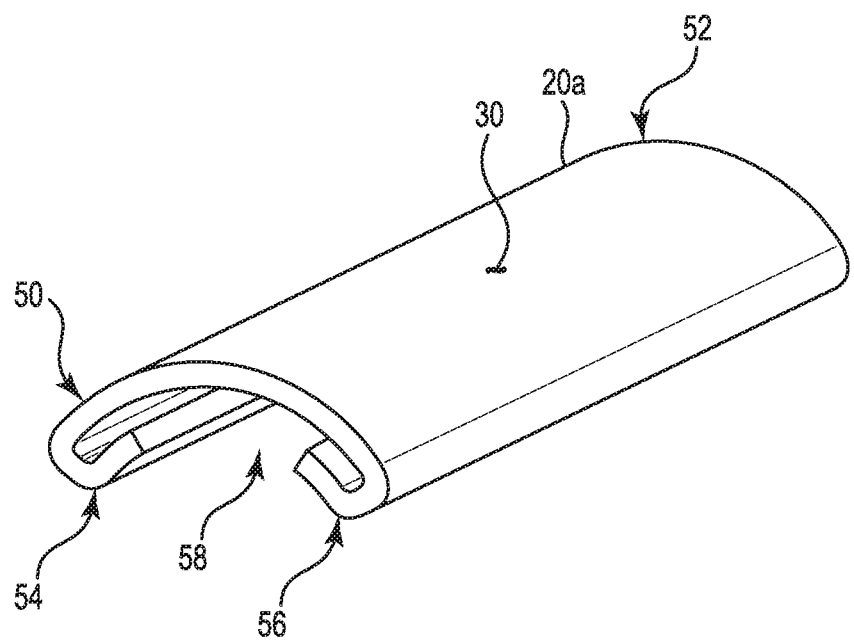
FIG. 6 illustrates a perspective view of one representative electrode segment in accordance with one illustrative embodiment.

One representative electrode segment 20a is illustrated in detail in FIG. 6. In this illustrative embodiment, the electrode segment 20a is made of a conductive material and includes a conducting section 30, a distal end 50 and a proximal end 52, as well as a first retaining feature 54 and a second retaining feature 56. The conducting section 30 of the electrode segment 20a is defined as a portion of each electrode segment 20a positioned outside of the catheter body 12 (see also, FIG. 5). In one example embodiment, the conducting section 30 is arcuate and corresponds to the curvature of catheter body 12. As indicated above, the contact surface of conducting section 30 defines an arc angle α less than 360°, less than a full circumference of the catheter body 12 so that each electrode (e.g., 20, 22, 24, 26) provided along a length of the catheter body 12 can include a plurality of segments (e.g., 20a, 20b). As indicated above, the arc angle α can, for example, be about 180°, 120°, 90° degrees or less) as is best shown in FIG. 5.

Each retaining feature 54, 56 is a flange or folded extension of the conducting surface of conducting section 30 and extends toward the opposing retaining feature 54, 56. In various embodiments, the retaining features 54, 56 and the conducting section 30 have a uniform material thickness. The conducting section 30 and retaining features 54, 56 collectively form a channel 58 in which the catheter body 12 is positioned during final assembly (see, in particular, FIG. 5). To secure each electrode segment 20a-b, 22a-b, 24a-b, 26a-b to the catheter body 12, the first retaining feature 54 is inserted into one respective slot (e.g., slot 42a). Then, the second retaining feature 56 is slid into a second slot (e.g., slot 42b) so that both retaining features 54, 56 are positioned within the slots 42a, 42b and center lumen 40, while the catheter body 12 is positioned within the channel 58. The assembly process continues in a similar manner until all desired electrode segments 20a-b, 22a-b, 24a-b, 26a-b of the catheter 10 are positioned within respective slots (e.g., 42a-d). As described above, in this particular embodiment, the electrode segment 20a is symmetrical. Optionally, one or more electrode segments 20a-b, 22a-b, 24a-b, 26a-b are then sealed to the catheter body 12 via welding, swaging and/or adhesive sealing processes.

In one embodiment, retaining features 54, 56 are flexible such that during assembly each can initially be directed toward the center of the lumen 40 of the catheter body 12. Once the respective electrode segment (20a-b, 22a-b, 24a-b, 26a-b, etc.) are in position, and retaining features 54, 56 are extending through respective slots 42a, 42b and into center lumen 40, retaining features 54, 56 can then be bent back against the interior surface of lumen 40, such as depicted in FIG. 5, for example.

In one embodiment, catheter body 12 is formed from a compliant material such that retaining features 54, 56 can be manipulated to extend into slots 42a, 42b without needing to bend the features 54, 56, but rather by moving and bending the catheter. In one embodiment, a combination of manipulating the catheter body 12 and bending the retaining features 54, 56 can be used.

Although slots 42a, 42b have been illustrated parallel to the axial length of catheter body 12, in other embodiment the slots can be oriented perpendicular thereto. In other embodiments the retaining features 54, 56 of the electrode segments (20a-b, 22a-b, 24a-b, 26a-b, etc.) can then be oriented on the distal end 50 and proximal end 52 in order to fit into the respective slots. In other embodiments, various combinations of parallel and perpendicular oriented slots can be used, as can other orientations.

In one embodiment, a biocompatible adhesive can be added between each conductive segment and the outer surface of the catheter body 12. Such adhesive can further secure the segments in place. Furthermore, more or less than two retaining features can be used with each electrode segment. For example, in FIG. 5 only retaining feature 54 may be used in one embodiment in conjunction with an adhesive to retain the conductive segment 20a in place on catheter body 12.

Although specific embodiments have been illustrated and described herein, it will be appreciated by those of ordinary skill in the art that a variety of alternate and/or equivalent implementations may be substituted for the specific embodiments shown and described without departing from the scope of the present disclosure. This application is intended to cover any adaptations or variations of the specific embodiments discussed herein. Therefore, it is intended that this disclosure be limited only by the claims and the equivalents thereof.

What is claimed is:

1. A method of assembling a medical catheter, the method comprising:
   providing a catheter body made of a compliant material, the catheter body having a center lumen;
   forming first and second slots within the catheter body;
   providing a first electrode having a plurality of electrode segments, each electrode segment including a contact surface interconnecting first and second retaining features;
   wherein the contact surface and the first and second retaining features collectively define a channel;
   inserting the first retaining feature within the first slot and into and inside the center lumen of the catheter body; and
   inserting the second retaining feature within the second slot and into and inside the center lumen so that the catheter body is positioned within the channel and the first and second retaining features extend into and inside the center lumen.

2. The method of claim 1 further comprising welding, swaging or adhering at least one electrode segment to the catheter body.

3. The method of claim 1, wherein the contact surface defines an arc angle between about 90 and about 180 degrees of a circumference of the catheter body, wherein the contact surface is positioned outside the catheter body and in contact with an outer surface of the catheter body and at least the first and second retaining features are positioned inside the center lumen and at least partially against an interior surface of the center lumen.

4. The method of claim 1, wherein four slots are formed around a circumference of the catheter body for each electrode.

5. The method of claim 1, wherein the catheter body includes a distal end and further wherein a first electrode segment of the plurality of electrode segments and a second electrode segment of the plurality of electrode segments are positioned an equal distance from the distal end.

6. The method of claim 1 further comprising providing a plurality of electrodes and securing each of the plurality of electrodes within slots provided in the catheter body.

7. The method of claim 1 further comprising a wire assembly operatively connected to the first electrode.

8. The method of claim 7, wherein the wire assembly is routed through the center lumen.

9. The method of claim 1, wherein the first retaining feature and the second retaining feature are symmetrical with respect to each other.

10. The method of claim 1, wherein the first and second retaining features are each a flange.

11. A medical catheter comprising:
    a catheter body made of a compliant material;
    the catheter body having a center lumen and including first and second slots; and
    a first electrode having a plurality of electrode segments, each electrode segment including first and second retaining features and a contact surface interconnecting the first and second retaining features;
    wherein the contact surface and the first and second retaining features collectively define a channel;
    wherein the first retaining feature is within the first slot and inside the center lumen of the catheter and the second retaining feature is within the second slot and inside the center lumen so that the catheter body is positioned within the channel and the first and second retaining features extend into and inside the center lumen.

12. The medical catheter of claim 11, wherein the medical catheter is an electrophysiology catheter, wherein at least the contact surface is positioned outside the catheter body and at least the first and second retaining features are positioned inside the center lumen.

13. The medical catheter of claim 11, wherein a material thickness of the contact surface and the first retaining feature is uniform, each of the plurality of electrode segments extend a portion of a circumference of the catheter body, and at least the contact surface is positioned outside the catheter body and in contact with an outer surface of the catheter body and at least the first and second retaining features are positioned inside the center lumen and at least partially against an interior surface of the center lumen of the catheter body.

14. The medical catheter of claim 11, wherein four slots are formed around a circumference of the catheter body for the first electrode.

15. The medical catheter of claim 11, wherein the catheter body has an outer diameter of 0.0945 inches or less.

16. The medical catheter of claim 11, further comprising a plurality of electrodes, wherein the first electrode is among the plurality of electrodes.

17. The medical catheter of claim 11, wherein the compliant material is polyether block amide.

18. The medical catheter of claim 11, further comprising a wire assembly operatively connected to the first electrode through an aperture in the catheter body, the wire assembly being routed through the center lumen of the catheter body to the first electrode.

19. The medical catheter of claim 11, wherein the first retaining feature and the second retaining feature are symmetrical with respect to each other and are flexible such that the first and second retaining features are bendable to position against an interior surface inside the center lumen of the catheter body.

20. The medical catheter of claim 11, wherein the first and second retaining features are each a flange that extend toward each other, and the contact surface is positioned outside the catheter body and proximate to an outer surface of the catheter body.

\* \* \* \* \*